United States Patent [19]

O'Neil

[11] Patent Number: 4,652,259

[45] Date of Patent: Mar. 24, 1987

[54] CATHETER ASSEMBLY

[76] Inventor: Alexander G. B. O'Neil, 102 Lawler Street, Subiaco 6008, Perth, Australia

[21] Appl. No.: 714,671

[22] Filed: Mar. 21, 1985

Related U.S. Application Data

[63] Continuation-in-part of Ser. No. 598,401, Apr. 10, 1984, abandoned, which is a continuation of Ser. No. 284,647, Jul. 20, 1981, abandoned, which is a continuation of Ser. No. 74,659, Sep. 12, 1979, abandoned.

[51] Int. Cl.⁴ .............................................. A61M 25/00
[52] U.S. Cl. ..................................... 604/54; 128/768; 604/171
[58] Field of Search ............................... 604/171-172, 604/280-282, 271, 54; 128/756, 759, 768

[56] References Cited

U.S. PATENT DOCUMENTS

| 3,421,509 | 1/1969 | Fiore | 604/171 |
| 4,023,559 | 5/1977 | Gaskell | 128/759 |
| 4,062,363 | 12/1977 | Bonner | 604/171 |

Primary Examiner—Dalton L. Truluck
Attorney, Agent, or Firm—Mason, Fenwick & Lawrence

[57] ABSTRACT

A urinary catheter assembly having a catheter tube disposed within an outer sheath, a closure member being provided over the distal end of the sheath. Penetration of the catheter assembly into the urethra is limited by the provision of a stop member extending outwardly from the sheath and spaced from the sheath's distal end by a specific distance to allow the sheath to pass bacteria in the outer portion of the urethra, but penetrate no further.

9 Claims, 6 Drawing Figures

CATHETER ASSEMBLY

This application is a continuation-in-part of U.S. patent application Ser. No. 598,401 filed Apr. 10, 1984, which is a continuation of Ser. No. 284,647, filed on July 20, 1981 and which is a continuation of Ser. No. 074,659, filed on Sept. 12, 1979, all of which are now abandoned.

BACKGROUND OF THE INVENTION

This invention relates to improvements in medical instruments, and more particularly to urinary catheters.

One of the most common medical procedures is the insertion of a medical instrument into a body passage, for example the insertion of a catheter through the urethra into the bladder, and, despite great advances having been made in the prevention of infection in many areas, this procedure has continued to cause introduction of infection into the bladder.

It is standard practice for catheterisation to be performed only after the area around the urethra has been thoroughly cleaned, the catheter has been sterilised and the operator has donned surgical gloves and mask, and yet infection has still been common. The reason for this has now been deduced as resulting from bacteria which are present within the urethra itself particularly at its outer end, and which it is difficult if not impossible to remove prior to insertion of the catheter. As the catheter enters the urethra, therefore, it comes into contact with the bacteria and carries them along the urethra and into the bladder, thus causing infection. No amount of precleaning of the area external of the urethra will prevent this.

Several proposals have previously been made to prevent the catheter carrying bacteria along the body passage, but none of these have proved entirely successful. For example, U.S. Pat. Nos. 3,332,424 (Minteer), 3,908,635 (Vick) and 3,908,663 (Vick) describe catheters having a tube of thin flexible material and a rigid collar secured around one end of the catheter tube. In use, these catheters are operated by placing the collar around the entrance to the body passage and pushing the tube through the collar so that the tube progressively everts along the passage. In this way movement of the tube wall relative to the passage wall is reduced so that bacteria are less likely to be carried along the passage, but bacteria can nevertheless be forced into the leading open end of the tube as it everts. These bacteria are then redeposited further up the passage on continued eversion of the tube. While these previously proposed catheters are an improvement over a basic catheter tube they still cause a degree of contamination by carrying bacteria further up the passage.

U.S. Pat. No. 3,669,099 (Silverman) describes and claims a similar system to the above-described prior art in that it has everting tubing for contacting a body cavity wall, but in this case the ends of the tubing are secured and sealed to a rigid cylindrical tube surrounding the tubing, so that the tubing forms a closed toroidal chamber which is then filled with a fluid. A long cylindrical medical instrument can then be pushed through the tubing, and the pressure of fluid causes the tubing to evert as the instrument passes through it. This previously-proposed arrangement is complex as a fluid inlet must be provided in the rigid tube for injection of fluid to an appropriate pressure, and the presence of the toroidal chamber makes the apparatus rather wide and therefore somewhat uncomfortable for the patient. It is also relatively expensive to manufacture.

U.S. Pat. No. 3,421,509 (Fiore) and West German Offenlegungsschrift No. 24 56 980 both have a urethral catheter in which the catheter tube is slidable within an impervious-walled sheath having a closure member in the form of overlapping flaps at its distal end. The sheath also has an external shoulder for engaging the mouth of the urethra to limit the extent of insertion of the sheath into the urethra. In Fiore the shoulder is stated to be about 1.5 inches from the distal end of the sheath.

U.S. Pat. No. 4,023,559 (Gaskell) also has a catheter tube slidable within an impervious-walled sheath which has a closure formation at its distal end through which the catheter tube can extend. No limiting shoulder is provided on the sheath to determine its extent of penetration.

SUMMARY OF THE INVENTION

The inventor in the present case has discovered that a pressure gradient exists along the urethra, the pressure increasing from each end to a maximum mid-way along the urethra as illustrated in FIG. 1 of the accompanying drawings. This gradient provides a natural barrier to passage of bacteria upwardly along the urethra, since the bacteria cannot normally pass the high-pressure area and are therefore retained in the lower part of the urethra.

However, introduction of a conventional catheter along the urethra causes bacteria to be carried past the high-pressure area and into the sterile upper urethra and bladder, causing infection. The passage of the catheter thus breaks down the natural barrier to bacteria.

The present invention provides a urinary catheter assembly for use in inserting a catheter through a urethra into a bladder, the urethra being contaminated with bacteria in an outer portion of its length, the assembly comprising a catheter, a hollow sheath having an impervious side wall, the sheath having a distal end, the catheter being slidable within the sheath, a flexible closure member on the distal end of the sheath, the closure member being normally closed and openable to allow passage of the catheter through it, and a stop member extending outwardly from the sheath for engaging an area around the entrance to a urethra on penetration of the sheath into the urethra to prevent further such penetration, the stop member being spaced from the distal end of the sheath by a distance equal to the distance of the high-pressure area from the lower end of the urethra.

In the present invention the stop member is provided for engaging the entrance to the urethra so as to limit the penetration of the closed hollow sheath so that its forward end extends only as far as the high-pressure area of the urethra but no further. Thus the sheath does not carry the bacteria into the upper, sterile area of the urethra, and the uninfected catheter emerges from the sheath and can pass into the bladder free of bacteria. The distance from the entrance of the urethra to the high-pressure area has been found to be constant in almost all patients, being about 1.5 cm in women, and the stop member is therefore positioned at that distance from the leading end of the sheath's closure member.

The distance of the stop member from the distal end of the sheath is crucial to the present invention as it must be the same as the distance from the mouth of the urethra to the high-pressure area within the urethra. If the stop member is closer to the distal end, the catheter tube on emerging from the sheath enters the lower, contaminated area of the urethra and thus carries bacteria past the high-pressure area and into the bladder, causing infection. If on the other hand the stop member is further from the distal end, the act of inserting the sheath into the urethra causes bacteria to be carried on the sheath from the lower area of the urethra past the high-pressure area; the pressure gradient in the upper part of the urethra then traps the bacteria and causes infection of the bladder.

The catheter assembly of the present invention has a relatively rigid outer sheath which facilitates handling of a relatively soft catheter which can be allowed to slide through it. The sheath acts as a splint so that it can be inserted directly into the urethra up to the point of maximum pressure. At the mid-urethral high pressure zone therefore the urethra can be opened by the sheath with its flexible closure member.

The combination of the relatively rigid sheath which facilitates handling and the flexible closure member provides an excellent seal which makes the design of the present invention unique. This combination greatly facilitates handling of the catheter and provides a very simple procedure for introducing the catheter. The sheath essentially provides a sterile sleeve and a splint which can be easily held by the operator while a soft flexible catheter slides through the flexible closure member.

In use, the sheath is inserted into a body passage to an extent whereby it penetrates to the urethra's high pressure area, which is slightly beyond bacteria within the passage adjacent its outer end, so that the catheter tube is isolated from such bacteria by the sheath. The catheter tube is then pushed through the closed end of the sheath to continue along the passage to the bladder, and in this way bacteria is not carried into the bladder by the catheter.

The stop means may be a portion of increased diameter, for example in the form of a collar, spaced from the distal end of the sheath to engage the area around the urethra entrance and thus limit the penetration of the sheath.

A very effective manner of providing the openable sheath end is for that end portion to be slit so that in its normal state the slit is closed to seal the sheath end, but when the distal end of the catheter is pressed against it from within the sheath the slit opens to define an aperture for passage of the catheter. For this to operate most effectively the sheath end portion should be resilient so that the slit closes again on retraction of the catheter into the sheath; bacteria are therefore prevented from entering the sheath on removal of the assembly from the passage. In an alternative arrangement the sheath can have a membrane across its end, the membrane being rupturable on pushing the catheter against it.

For ease of insertion as well as for effective sealing, the end portion of the sheath is preferably tapered.

The sheath may be in one piece or may alternatively comprise a number of parts which together produce the desired features. For example the sheath may have an open-ended tubular body portion within which the catheter slides, and a cap enveloping one end of the body portion and having an openable closed end. In any event it is preferable that the sheath should be sufficiently long to allow it in use to be held externally of the urethra thus making the assembly easy to use.

The assembly of this invention can also be modified to allow its use without the necessity for the user to wear surgical gloves and other protective clothing, by making the sheath longer than the portion of the instrument for insertion into the urethra, so that that portion of the catheter is contained within the sheath before use. In this way the user will handle the catheter only in areas which will not enter the passage, so bacteria will not be transferred into the urethra from the user's hands by the catheter.

To further ensure the isolation of bacteria a second sheath can be provided movable with the catheter and connected with the first sheath in a manner allowing relative longitudinal movement between them while retaining between them a barrier against passage of bacteria to the catheter. The sheaths may be connected in a telescopic arrangement with one of the sheaths being slidable within the other. Alternatively a collapsible connection may extend between them, for example a "concertina" connection. The second sheath may be secured to the catheter so as to be permanently movable with it, or it may be of flexible material so that the catheter can be gripped through the second sheath by applying finger pressure.

Embodiments of the invention will now be described by way of example with reference to the accompanying drawings, in which:

DESCRIPTION OF THE PREFERRED EMBODIMENTS

Figure 1:
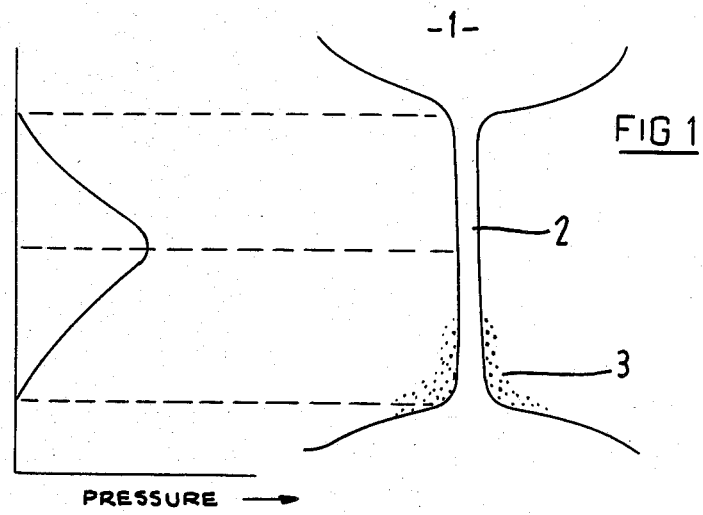
FIG. 1 is a schematic diagram showing the distribution of bacteria in a female urethra and the natural exertion of pressure on the urethra wall.

Referring to FIG. 1, the bladder 1 communicates with the outside through the urethra 2. The bladder 1 and upper urethra 2 are sterile, but the lower urethra and the area surrounding it are highly contaminated by bacteria 3. As can be seen from the associated distance/pressure graph of FIG. 1 a pressure gradient exists within the urethra, the pressure increasing from both ends to a maximum at the position X. The high pressure at X provides a natural barrier to bacteria, maintaining them in the lower urethra and thus protecting the upper urethra and bladder from contamination. The high-pressure barrier at X is spaced about 1.5 cm from the mouth of the urethra.

When the bladder is to be drained by catheterisation the external area around the urethra 2 is thoroughly cleaned but it is very difficult to clean the lower urethra internally so a considerable amount of bacteria 3 remain. Insertion into the urethra 2 of an unprotected catheter therefore causes the bacteria 3 to be carried past the high-pressure barrier at X and taken further along the urethra 2, thus contaminating the upper urethra and bladder if the instrument is inserted sufficiently far.

Figure 3:
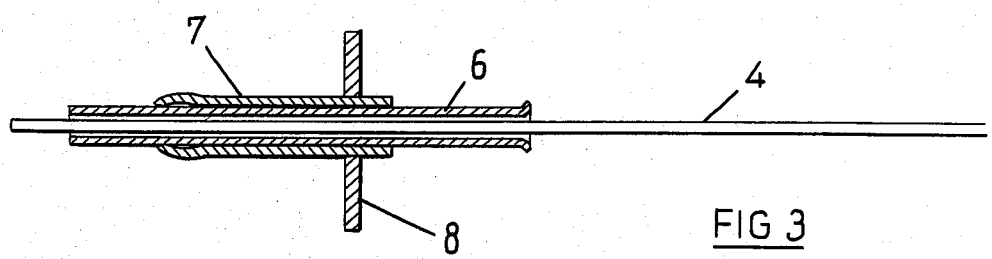
FIG. 3 is a side sectional view of the catheter and introducer of FIG. 2 in use.
Figure 4:
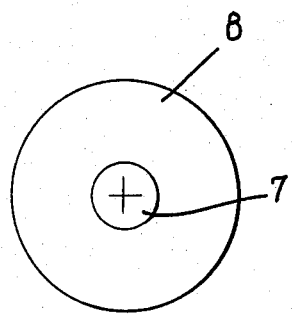
FIG. 4 is an end elevation corresponding to FIG. 2.
Figure 5:
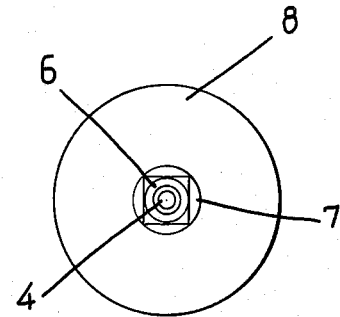
FIG. 5 is an end elevation corresponding to FIG. 3.

Referring now to FIGS. 2 to 5, the problem of bacteria 3 being carried along the urethra 2 is obviated or mitigated by providing a catheter tube 4, of conventional flexible plastics material, within a sheath 5 whose side walls are impervious to bacteria and which is more rigid than the catheter tube 4. The sheath 5 is formed by a plastics outer tube 6 coaxial with the catheter tube 4 and having over its distal end a flexible latex rubber cover 7. The distal end of the cover 7 is cross-cut so as to provide a seal against passage of bacteria when in its closed position as in FIGS. 2 and 4, while allowing penetration of the outer tube 6 and catheter tube 4 on application of pressure by them, as shown in FIGS. 3 and 5. An annular rubber collar 8 fits over the cover 7 and outer tube 6 at a distance of 1.5 cm from the distal end of the cover 7.

In use, the catheter is inserted, cover 7 first, into the urethra 2 until the collar 8 abuts the area around the urethra entrance and prevents further penetration; at this stage the cross-cut end of the cover is at the high-pressure area marked X in FIG. 1, but no further. As the collar 8 is spaced from the ends of the sheath 5 the sheath can still be easily gripped by the user when fully inserted into the urethra, by holding the outer tube 6. The outer tube 6 is then pushed through the cross-cut end of the cover 7 to extend further into the urethra but not to penetrate into the bladder 1. Because of the closed end of the cover 7 during initial insertion bacteria are not transferred to the outer tube 6 to any significant degree as it extends through the cover 7. The bacteria 3 are thus retained below the high-pressure area X.

In the final stage of insertion the catheter tube 4 is pushed through the outer tube 6 and into the bladder 1. The bladder 1 can then be drained without risk of infection.

Instead of pushing the outer tube 6 through the cross-cut end of the cover 7, the catheter tube 4 may be pushed straight into the bladder 1 through the cross-cut end. In this way there is a slightly greater risk of bladder infection but in fact it is insignificant. The inner diameter of the outer tube 6 is the same as the outer diameter of the catheter tube 4 or slightly less, and in this way the catheter tube 4 is retained in the outer tube 6 and will not fall out during use.

It is also of importance in this embodiment of the invention that the outer tube 6 should be of greater length than the maximum distance through which the catheter tube 4 will project in use from the cover 7. In this way contamination of the catheter tube 4 externally of the outer tube 6 will not be transferred along the outer tube 6 and into the urethra 2 or bladder 1. Further, when the catheter is used in the manner described above, the outer tube 6 should not be pushed through the cover 7 by an extent greater than the length of the cover. This further prevents any bacteria being transferred into the bladder or urethra.

Figure 6:
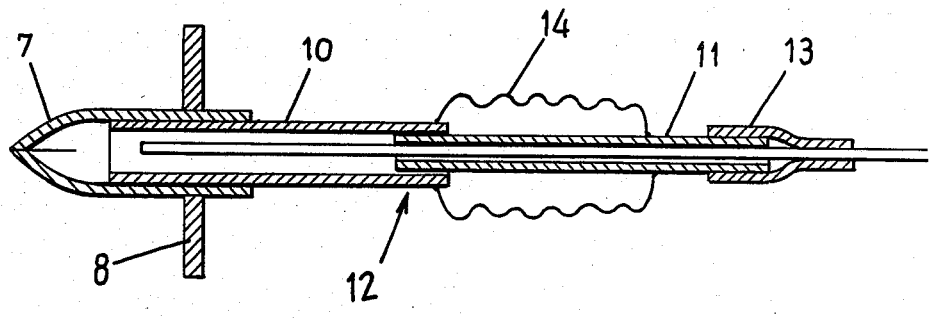
FIG. 6 is a side sectional view of a further alternative form of a urethral catheter and introducer, in accordance with the invention.
Figure 2:
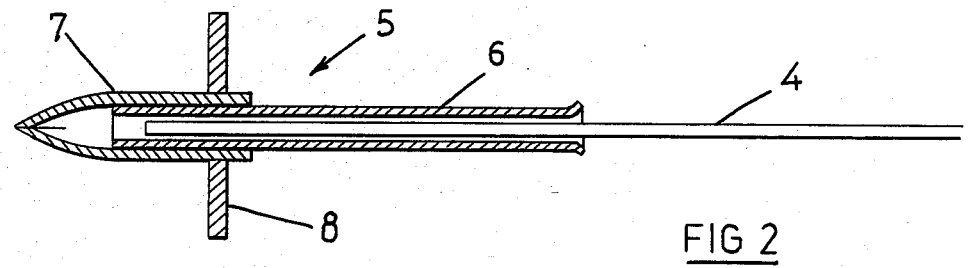
FIG. 2 is a side sectional view of a catheter with its introducer, in accordance with the invention.

Referring now to FIG. 6, the catheter tube 4 has two outer tubes 10 and 11 disposed coaxially around it. The second outer tube 11 is of smaller diameter than the first outer tube 10 and extends into it in telescopic fashion at 12. The first tube 10 has at its opposite end a rubber cover 7 held on the first tube 10 by a rubber collar 8 which also acts as a stop member as in FIGS. 2 to 5; the cover 7 is cross-cut at its distal end.

The free end of the second sheath 11 is secured to the tube 4 by a tight-fitting sleeve 13 which prevents relative movement between the tube 4 and sheath 11.

The sheaths 10 and 11 are made of rigid plastics material while the tube 4 is of pliable plastics material and the cover 7 is of soft rubber.

The instrument of FIG. 6 is used in similar fashion to those of FIGS. 2 to 5, except that the catheter tube 4 is not handled directly, being protected by the tubes 10 and 11. When the catheter tube 4 is to be pushed through into the urethra this is achieved by gripping and pushing the second tube 11 into the first tube 10.

The rigidity of the outer tubes 10 and 11 allows the pliable tube 4 to be easily introduced. A thin plastics cover 14 is secured to both outer tubes 10 and 22 to prevent bacteria entering between the tubes and thus contaminating the tube 4.

I claim:

1. A urinary catheter assembly for use in inserting a catheter through a urethra into a bladder, the urethra being contaminated with bacteria in an outer contaminated portion of its length, the assembly comprising
   a catheter,
   a hollow sheath having an imprevious side wall,
   the sheath having a distal end,
   the catheter being slideable within the sheath,
   a flexible closure member on the distal end of the sheath,
   the closure member being normally closed and openable to allow passage of the catheter through it,
   and a stop member extending outwardly from the sheath for engaging an area around the entrance to a urethra on penetration of the sheath into the urethra to prevent penetration of the distal end of the sheath inwardly by an said outer contaminated portion of the urethra,
   the stop member being spaced from the distal end of the sheath by a distance of about 1.5 cm.

2. An assembly according to claim 1, wherein the sheath comprises a rigid open-ended sleeve within which the catheter is slideable and the closure member is a cap enveloping one end of the sleeve, the cap being normally closed but being openable to allow passage of the catheter through it.

3. An assembly according to claim 1, wherein the distal end of the sheath is resilient and is slit so that in its normal state the slit is closed but is openable on pressure from within the sheath to define an aperture.

4. An assembly according to claim 1, wherein the stop member is in the form of a collar extending radially outwardly from the sheath.

5. A catheter assembly according to claim 1, wherein a second sheath is provided movable with the catheter and connected with the first sheath in a manner allowing relative longitudinal movement between them while retaining between them a barrier against passage of bacteria.

6. A method of removing fluid from a human by catheterisation through a urethra having an upper and a lower end and having a side wall on which natural body pressure is exerted in a direction constricting the urethra, said pressure increasing from said upper and lower ends to a maximum value at a known position intermediate said ends said urethra being bacteria contaminated below said known position, said method comprising:
   providing a catheter assembly having a catheter, a hollow sheath having an imprevious side wall, the sheath having a distal end and the catheter being slideable within the sheath, a flexible closure member on the distal end of the sheath, the closure member normally closed and openable to allow passage of the catheter through it, and a stop member extending outwardly from the sheath at a location spaced from the distal end of the sheath equal to the distance between the position of maximum pressure and the lower end of the urethra, inserting the distal end of the sheath into the urethra with the flexible closure member in its closed position, passing the sheath along the urethra until the stop member engages an area around the entrance to the urethra, sliding the catheter through the sheath so that it passes through the closure member and enters the bladder without bacteria contamination, and allowing fluid to flow from the bladder through the catheter.

7. A method according to claim 6, wherein the sheath is moved a distance of approximately 1.5 cm into the urethra.

8. A method of positioning the distal end of a catheter in a human bladder by movement through a urethra having an upper and a lower end and having a side wall on which natural body pressure is exerted in a direction constricting the urethra, said pressure increasing from said upper and lower ends to a maximum value at a known position intermediate said ends said urethra being bacteria contaminated below said known position, said method comprising the steps of:

providing a catheter assembly having a catheter positioned in a hollow sheath having an impervious side wall, the sheath having a distal end and the catheter being slideable with the sheath, the closure member normally closed and openable to allow passage of the catheter through it, inserting the distal end of the sheath into the lower end of the urethra with the flexible closure member in its closed position, moving the sheath along the urethra so that the distal end of the sheath is in said known position of maximum pressure but does not go beyond said known position, sliding the catheter through the sheath so that it passes through the closure member into the portion of the urethra upwardly of said known position but does not contact the urethra downwardly of said known position and enters the bladder without bacteria contamination.

9. A method according to claim 8, wherein the sheath is retained in position in the urethra while the catheter is withdrawn from the bladder and into the sheath, and thereafter the sheath is withdrawn from the urethra.

* * * * *

UNITED STATES PATENT AND TRADEMARK OFFICE
CERTIFICATE OF CORRECTION

PATENT NO. : 4,652,259

DATED : March 24, 1987

INVENTOR(S) : Alexander G.B. O'Neil

It is certified that error appears in the above-identified patent and that said Letters Patent is hereby corrected as shown below:

On the cover page, field [63] Related U.S. Application Data, that portion of the Related U.S. Application Data reading "Apr. 10, 1984," should read --Apr. 9, 1984,--.

Signed and Sealed this

Eleventh Day of January, 1994

Attest:

BRUCE LEHMAN

Attesting Officer

Commissioner of Patents and Trademarks